(12) United States Patent
Nadeem et al.

(10) Patent No.: US 12,331,073 B2
(45) Date of Patent: Jun. 17, 2025

(54) PREPARATION OF BIOLOGICALLY ACTIVE COMPLEXES

(71) Applicant: HAMLET PHARMA AB, Lund (SE)

(72) Inventors: Aftab Nadeem, Lund (SE); Catharina Svanborg, Malmo (SE); Chin Shing Ho, Lund (SE)

(73) Assignee: HAMLET PHARMA AB, Lund (SE)

( * ) Notice: Subject to any disclaimer, the term of this patent is extended or adjusted under 35 U.S.C. 154(b) by 0 days.

(21) Appl. No.: 17/146,588

(22) Filed: Jan. 12, 2021

(65) Prior Publication Data

US 2021/0130394 A1   May 6, 2021

Related U.S. Application Data

(62) Division of application No. 16/612,272, filed as application No. PCT/EP2018/062396 on May 14, 2018, now abandoned.

(30) Foreign Application Priority Data

May 14, 2017 (GB) ...................... 1707715

(51) Int. Cl.
| | |
|---|---|
| C07K 1/107 | (2006.01) |
| A61K 38/00 | (2006.01) |
| A61P 35/00 | (2006.01) |
| C07K 1/34 | (2006.01) |
| C07K 14/76 | (2006.01) |

(52) U.S. Cl.
CPC ............. *C07K 1/107* (2013.01); *A61P 35/00* (2018.01); *C07K 1/34* (2013.01); *C07K 14/76* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 8,796,218 B2 | 8/2014 | Svanborg et al. | |
| 2012/0028883 A1 | 2/2012 | Svanborg et al. | |
| 2015/0216945 A1 | 8/2015 | Svanborg et al. | |
| 2020/0140481 A1 | 5/2020 | Nadeem et al. | |

FOREIGN PATENT DOCUMENTS

| | | |
|---|---|---|
| JP | 2019563219 A | 7/2020 |
| WO | 2010/079362 A1 | 7/2010 |
| WO | 2010/131010 A2 | 11/2010 |
| WO | 2010/131237 A1 | 11/2010 |
| WO | 2012/069836 A2 | 5/2012 |
| WO | 2014/023976 A1 | 2/2014 |
| WO | WO 2014/023976 * | 2/2014 |
| WO | 2018/116165 A2 | 6/2018 |
| WO | 2018/210759 A1 | 11/2018 |

OTHER PUBLICATIONS

Edmondson et al. (Journal of Dairy Science. vol. XXXIX, No. 2, Feb. 1956) (Year: 1956).*
Svensson et al. (Proc Natl Acad Sci USA. Apr. 11, 2000;97(8):4221-6) (Year: 2000).*
GB Search Report for Application No. GB1707715.7, dated Feb. 19, 2018; 4 pgs.
International Search Report and Written Opinion for International Application No. PCT/EP2018/062396, dated Aug. 27, 2018; 14 pgs.
Svensson et al., "Conversion of α-lactalbumin to a protein inducing apoptosis", PNAS, 2000, pp. 4221-4226, vol. 97, No. 8.
Vukojevic et al., "Lipoprotein Complex of Equine Lysozyme with Oleic Acid (ELOA) Interactions with the Plasma Membrane of Live Cells", Langmuir, 2010, pp. 14782-14787, vol. 26, No. 18.
Tatsuro Kamijima et al., Heat-treatment method for producing fatty acid-bound alpha-lactalbumin that induces tumor cell death, Biochemical and Biophysical Research Communications, vol. 376, Issue 1, Nov. 7, 2008, pp. 211-214.
Office Action mailed Apr. 26, 2022 in Japanese Application 2019-563219.

* cited by examiner

*Primary Examiner* — Sergio Coffa
(74) *Attorney, Agent, or Firm* — POLSINELLI PC (57) ABSTRACT

The invention provides a method for preparing a biologically active complex, said method comprising dissolving a mixture of a polypeptide element, such as alphalactalbumin or fragments thereof, in powder form and oleic acid or a pharmaceutically acceptable salt thereof also in solid form, in an aqueous solvent comprising a mixture of at least two and preferably three salts, wherein the method is carried out at moderate temperatures. The preparation does not require extensive heating and so is simple and efficient to carry out.

11 Claims, 4 Drawing Sheets
Specification includes a Sequence Listing.

PREPARATION OF BIOLOGICALLY ACTIVE COMPLEXES

CROSS-REFERENCE TO RELATED APPLICATIONS

This application is a divisional of U.S. patent application Ser. No. 16/612,272, filed Nov. 8, 2019, which is a U.S. National Stage Application of International Application No. PCT/EP2018/062396, filed May 14, 2018, which claims the benefit of, and priority to Great Britain Patent Application No. 1707715.7, filed May 14, 2017, the entire contents of which are hereby incorporated by reference in their entirety.

SEQUENCE LISTING

This application contains a Sequence Listing that has been submitted in ASCII format via EFS-Web and is hereby incorporated by reference in its entirety. The ASCII copy, created on May 14, 2017, is named P3387PC00_SeqList.txt, and is 4 kilobytes in size.

FIELD OF THE INVENTION

The present invention relates to methods for preparing biologically active complexes that have therapeutic activity in particular in the treatment of tumours or as antibacterial or antiviral agents. The present invention further relates to methods of treating tumors and cancers, in particular to methods for selectively targeting tumor cells in preference to healthy cells, as well as to novel complexes and compositions for use in these methods.

BACKGROUND

There has been much interest in the production of complexes that involve partially unfolded proteins and lipids. These proteins may have drastically different properties and particularly biological properties than the corresponding proteins in a fully folded state. The gain of new, beneficial function upon partial protein unfolding and fatty acid binding is a remarkable phenomenon, and may reflect a significant generic route of functional diversification of proteins via varying their conformational states and associated ligands. Thus, in addition to alternative splicing of mRNA transcripts, post-translational modifications and changes in tertiary structure of specific domains, partial unfolding of a previously native protein is becoming recognized as a mechanism to generate functional diversity. This may be due to a cellular response to unfolded proteins and to the lipid cofactor, which defines their altered properties. However, this response may be different in for instance tumour cells, which means that they may give rise to therapeutic potential. In order to form stable moieties, the unfolded proteins are frequently modified in some way, and in particular may be bound to cofactors such as fatty acid cofactors. The complexes formed in this way may be stable and give rise to therapeutic options.

HAMLET (human alpha-lactalbumin made lethal to tumor cells) is one such example of a new family of tumoricidal molecules, with remarkable properties. Formed from partially unfolded α-lactalbumin and with oleic acid as an integral constituent, HAMLET was discovered by serendipity when studying the ability of human milk to prevent bacteria from binding to cells. Early in vitro experiments showed that HAMLET displays broad anti-tumor activity with a high degree of tumor selectivity and subsequent therapeutic studies have confirmed HAMLET's tumoricidal activity and relative selectivity for tumor tissue in vivo. In a placebo controlled clinical study, topical HAMLET administration removed or reduced the size of skin papillomas and in patients with bladder cancer, local instillations of HAMLET caused rapid death of tumor cells but not of healthy tissue surrounding the tumor. Therapeutic efficacy of HAMLET in bladder cancer was recently demonstrated in a murine bladder cancer model and HAMLET treatment delayed tumor progression and led to increased survival in a rat glioblastoma xenograft model without evidence of cell death in healthy brain tissue. HAMLET thus appears to identify death pathways that are conserved in tumor cells, thereby distinguishing them from healthy, differentiated cells.

Other complexes using equine lysozyme and oleic acid have also been found to produce cell death (Vukojevic et al. Langmuir, 2010, 26(18) 14782-14787), suggesting that different, unfolded proteins can become cytotoxic when coupled to a suitable cofactor.

Other work focuses on the use of peptide fragments of these proteins which may also be used (see for example EP-B-2643010 and co-pending British Patent application no 1621752.3.

Classically, these types of complex were prepared as described by Svensson et. Al (2000). Proc Natl Acad Sci USA 97, 4221-4226. Native α-lactalbumin was purified from human milk by hydrophobic interaction chromatography. The protein was unfolded with EDTA, subjected to ion-exchange chromatography on a matrix pre-conditioned with oleic acid and eluted with high salt, specifically 1M NaCl to obtain biologically active complexes. Procedures of this type have been used to produce other biologically active complexes including BAMLET, from bovine alpha-lactalbumin, and complexes formed from recombinant forms of alpha-lactalbumin, in particular those without cysteine residues as described in WO 2010/079362.

An alternative preparation for such biologically active complexes is described in WO2010/131010. In this reference, BAMLET is prepared in a one-phase system, in which α-lactalbumin is reconstituted in phosphate buffered saline (PBS) and sodium oleate added. The mixture is then heated to temperatures at or above 60° C. and active complex obtained. This method has the advantage of being simple to carry out, and may even be carried out in-situ in a clinical situation with the assistance of kits.

In other references, biologically active complex is prepared by dissolution of previously lyophilized complex in PBS (see for example WO2010/079362) for use.

Thus it is clear that complexes of this type rely on the presence of salts in their production. Phosphate buffered saline (PBS) as used previously, comprises a mixture of at least three and sometimes four salts. These are sodium chloride, disodium phosphate and mono-potassium phosphate, as well as in some cases also, potassium chloride.

The applicants investigated the impact of the salt mix used in the preparation of the compound and surprisingly found that the precise nature of the salts used in the production can impact on the activity of the product. This suggests that the products may be distinguished and therefore those with a specific salt balance are unique products.

SUMMARY OF THE INVENTION

According to the present invention there is provided a method for preparing a biologically active complex, said method comprising dissolving a mixture of a polypeptide element in powder form and oleic acid or a pharmaceutically acceptable salt thereof also in solid form, in an aqueous solvent comprising at least two salts, the first of which is sodium or potassium chloride and the second of which is disodium phosphate or mono-potassium phosphate, wherein, in particular, the method is carried out at moderate temperature.

As used herein, the expression 'moderate temperature' refers to temperatures of up to 50° C., for example from 0-50° C., for example from 10-40° C., and more particularly from 15-25° C., such as at ambient temperature. Such temperatures are generally below the 'melt temperature' at which the polypeptides become unfolded or denatured. However, the applicants have found that they are still able to form biologically active complexes under these salt conditions.

The applicants have found that active complex can be prepared which shows a clear dose-dependent response, by the simple dissolution method of the invention. Although the mixture may be warmed for example to temperatures of up to 50° C., such as up to 40° C. to achieve rapid dissolution, there is no need to heat the solution extensively such as described in by boiling, provided only that a suitable salt balance is present in the aqueous solvent. Thus in a particular embodiment, the method is carried out at ambient temperature.

Dissolution may be facilitated by agitation, for example by vortexing. If required, the solution may be filtered through a sterile filter at this stage. Suitable filters include polyethersulfone membranes (PES) or Minisart® NML Cellulose acetate membranes.

Any such agitation processes will be carried out for a period of time sufficient to ensure the dissolution of the elements in the salt solution. Although the precise timings may vary depending upon factors such as the particular nature of the polypeptide being used and the temperature at which the mixture is held, the timings will typically be quite short, for example no more than 10 minutes, for example from 1-5 minutes such as about 2 minutes.

In a particular embodiment, the solvent further comprises a third salt which is mono-sodium or mono-potassium phosphate, and in particular is mono-potassium phosphate. Such mixtures are found in conventional PBS solutions.

This method is therefore easy to prepare in a variety of manufacturing and non-manufacturing environments.

The term "polypeptide" used herein includes proteins and peptides including long peptides.

Suitable "polypeptide elements" for use in the method of the invention include naturally-occurring proteins, in particular alpha-lactalbumin, lysozyme or other proteins having a membrane perturbing activity, recombinant proteins and in particular variants of said naturally-occurring proteins which lack intra-molecular bonds for example as a result of mutation of cysteine residues, or in particular, fragments of any of these proteins, in particular peptides of up to 50 amino acids.

The expression "variant" refers to proteins or polypeptides having a similar biological function but in which the amino acid sequence differs from the base sequence from which it is derived in that one or more amino acids within the sequence are substituted for other amino acids. Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation.

Non-conservative substitutions are possible provided that these do not interrupt the function of the DNA binding domain polypeptides.

Broadly speaking, fewer non-conservative substitutions will be possible without altering the biological activity of the polypeptides.

Determination of the effect of any substitution (and, indeed, of any amino acid deletion or insertion) is wholly within the routine capabilities of the skilled person, who can readily determine whether a variant polypeptide retains the fundamental properties and activity of the basic protein. For example, when determining whether a variant of the polypeptide falls within the scope of the invention, the skilled person will determine whether complexes comprising the variant retain biological activity (e.g. tumour cell death) of complexes formed with unfolded forms of the native protein and the polypeptide has at least 60%, preferably at least 70%, more preferably at least 80%, yet more preferably 90%, 95%, 96%, 97%, 98%, 99% or 100% of the native protein.

Variants of the polypeptide may comprise or consist essentially of an amino acid sequence with at least 70% identity, for example at least 75%, 80%, 85%, 90%, 91%, 92%, 93%, 94%, 96%, 97%, 98% or 99% identity to a native protein sequence such as an alphalactalbumin or lysozyme sequence.

The level of sequence identity is suitably determined using the BLASTP computer program with the native protein sequences as the base sequence. This means that native protein sequences form the sequence against which the percentage identity is determined. The BLAST software is publicly available at http://blast.ncbi.nlm.nih.gov/Blast.cgi (accessible on 10 May 2017).

In a particular embodiment, the polypeptide element is a peptide that has no more than 50 amino acids, and in particular may have from 10-45 amino acids. Such complexes are easier to prepare and the starting materials are less costly. For instance, peptides may be prepared using conventional methods for the production of peptides. The complexes formed may be easier to handle and formulate for administration, due to the smaller molecular weight.

It is suitably derived from a naturally occurring protein or a variant thereof. Suitable proteins are those identified as being active in such complexes, such as alpha-lactalbumin, beta-lactoglobulin or lysozyme, but may be derived from any membrane perturbing proteins.

Membrane perturbing proteins are proteins which have the capability of interacting with the interface of cell membranes, in particular causing disruption such as tubulation of the cell membrane. Typically, the protein will become embedded in the cell membrane. Examples of such proteins include coat complexes such as COPI, COPII (such as SAR 1), HOPS/CORVET, SEA (Seh1-associated), and clathrin complexes BAR domain proteins such as endophilins, and the ESCRT complex, including Snf7 domain subunits.

In particular, the peptide is derived from the alpha-helical domain of a naturally occurring protein as described above. The alpha-helical domain of said proteins would be well understood in the art or may be determined using conventional methods.

Where the alpha-helical domain contains a cysteine residue, these may, in some embodiments, be modified to a different amino acid residue, such as an alanine residue, in order to avoid inter-molecular disulphide bonds.

In a particular embodiment, the peptide is a fragment of alpha-lactalbumin and specifically a fragment of the alpha domain of alpha-lactalbumin. In a particular embodiment, the peptide comprises amino acids of the Alpha 1 (residues 1-40) or Alpha 2 (residues 81-123) of human alpha-lactalbumin, or analogous regions of other alphalactalbumins such as bovine alpha-lactalbumin.

The peptide suitably contains no elements that give rise to folding and therefore suitably lacks amino acids that give rise to intramolecular bonding such as cysteine residues. In particular, where the peptide is derived from a naturally occurring protein, any cysteine residues are replaced by other amino acids such as alanine.

Thus in a particular embodiment, the complex comprises amino acids of the Alpha 1 (residues 1-40) or Alpha 2 (residues 81-123) of human alpha-lactalbumin wherein the cysteines are replaced with other amino acids such as alanine, to prevent any intra-molecular bonding.

Thus the peptide may be of SEQ ID NO 1 or SEQ ID NO 2

```
                                                 (SEQ ID NO 1)
KQFTKXELSQLLKDIDGYGGIALPELIXTMFHTSGYDTQA (SEQ ID NO 2)
LDDDITDDIMXAKKILDIKGIDYWLAHKALXTEKLEQWLXEKL
``` where X is an amino acid residue other than cysteine.

A particular example of such sequences are those of SEQ ID NO 3 or SEQ ID NO 4.

```
                                                 (SEQ ID NO 3)
KQFTKAELSQLLKDIDGYGGIALPELIATMFHTSGYDTQA (SEQ ID NO 4)
LDDDITDDIMAAKKILDIKGIDYWLAHKALATEKLEQWLAEKL.
```

In some cases, the peptides of SEQ ID NO 1 may be truncated, for example by omitting the terminal alanine residue, resulting in a peptide of SEQ ID No 6, of which SEQ ID NO 7 is a specific example.

```
                                                 (SEQ ID NO 6)
KQFTKXELSQLLKDIDGYGGIALPELIXTMFHTSGYDTQ (SEQ ID NO 7)
KQFTKAELSQLLKDIDGYGGIALPELIATMFHTSGYDTQ
```

Such peptides are novel and form a further aspect of the invention, together with biologically active complexes comprising them.

Other peptides may also be used in the complex and the suitability may be tested by determining whether complexes with a fatty acid salt are active, for instance in killing cells using methods as described hereinafter.

In another embodiment, the peptide is derived from a COPII family protein such as SAR1. A particular example of such a peptide is a peptide of SEQ ID NO 5

```
                                                 (SEQ ID NO 5)
MAGWDIFGWF RDVLASLGLW NKH.
```

In another embodiment, the polypeptide element is a naturally-occurring protein or a synthetic form thereof, in particular an alpha-lactalbumin, such as human, bovine, sheep, camel or goat alpha-lactalbumin. In particular, the protein is bovine lactalbumin.

As used herein, the term "biologically active" means that the complex has a biological activity, which is different from—or stronger than the individual components. In particular, the complex is able to induce cell death in particular selectively in tumour cells and/or has a bactericidal or antiviral effect not seen with the native protein including for example monomeric α-lactalbumin forms, although other therapeutic effects may be available.

In particular oleic acid used in the method of the invention is C18:1 oleic acid of formula $CH_3$ $(CH_2)_7CH=CH(CH_2)_7COOH$ or $CH_3$ $(CH_2)_7CH=CH(CH_2)_7COO^-$.

In a particular embodiment, a pharmaceutically acceptable salt of oleic acid is used in the process. Suitable pharmaceutically acceptable salts would be understood in the art.

Use of a salt, and in particular a water-soluble salt of the oleic acid, fatty acid or lipid means that the preparation method is facilitated since aqueous solutions may be formed for instance for application to ion exchange columns and the like. Suitable water-soluble salts are alkali or alkaline-earth metal salts such as sodium or potassium salts.

Furthermore, it has been found that salts and in particular oleate salts such as sodium oleate appear to have some inherent tumoricidal effect. Therefore the inclusion of this in the complex may give rise to activity increases.

In a particular embodiment, the first salt used in the method of the invention is sodium chloride.

In another particular embodiment, the second salt used in the method of the invention is disodium phosphate.

In another particular embodiment, the third salt used in the method of the invention is mono-potassium phosphate.

The ratio of first salt:second salt used in the method of the invention is suitably from 8:1 to 1:1, for example from 5:1 to 2:1 and in particular from 4:1 to 3.5:1. Where present the ratio of first salt:third salt is from 20:1 to 5:1, for example from 15:1 to 10:1 such as from 12.5:1 to 11.5:1.

In a particular embodiment the ratio of first to second to third salt is 13-12:4-3:1.

The ratio of oleic acid or oleate:peptide mixed in the method of the invention is suitably in the range of from 20:1 to 1 to 1, but preferably an excess of oleate is present, for instance in a ratio of oleate:peptide of about 5:1. The mixing can be carried out at a temperature of from 0-50° C., conveniently at ambient temperature and pressure.

If required, the product of the process of the invention may solidified for example by lyophilisation, for storage or for formulation purposes. Thereafter, it may be reconstituted using in particular, sterile water, for use. Such procedures may be particularly suitable where the polypeptide is a peptide rather than a protein. The applicants have found that proteins may revert to the natural folding state when subjected to procedures such as lyophilisation.

The problem may be alleviated by stabilising the polypeptide in the unfolded state, for example by lowering the pH of the solution, for instance to a value of 4 or less, or adding calcium chelators such as EDTA to the solvent during the preparation method. In a second aspect, the invention provides a complex obtainable by the method of the first aspect.

Thus, complexes of the second aspect of the invention may be formulated into useful pharmaceutical compositions by combining them with pharmaceutically acceptable carriers in the conventional manner. Such compositions form a third aspect of the invention.

The compositions in accordance with the third aspect of invention are suitably pharmaceutical compositions in a form suitable for topical use, for example as creams, ointments, gels, or aqueous or oily solutions or suspensions. These may include the commonly known carriers, fillers and/or expedients, which are pharmaceutically acceptable.

Topical solutions or creams suitably contain an emulsifying agent for the protein complex together with a diluent or cream base.

The daily dose of the complex varies and is dependent on the patient, the nature of the condition being treated etc. in accordance with normal clinical practice. As a general rule from 2 to 200 mg/dose of the biologically active complex is used for each administration.

In a further aspect of the invention, there is provided a method for treating cancer which comprises administering to a patient in need thereof, a biologically active complex as described above.

In particular, the complex may be used to treat cancers such as human skin papillomas, human bladder cancer and glioblastomas. In the latter case, administration may be by infusion as is known in the art.

The invention further provides the biologically active complex as defined above for use in therapy, in particular in the treatment of cancer.

The complex may also be of use in the prevention of cancer, in particular gastrointestinal cancer as described for example in WO2014/023976. In this case, the complex may be combined with a foodstuff, such as a dairy product such as yoghurt for use as a nutraceutical. Compositions of this type form a further aspect of the invention.

BRIEF DESCRIPTION OF THE DRAWINGS

The invention will now be particularly described by way of example with reference to the accompanying drawings, in which.

EXAMPLE 1

Production of Biologically Acceptable Complexes

A range of biologically active complexes were prepared using a peptide of SEQ ID NO 7

(SEQ ID NO 7)
Ac-KQFTKAELSQLLKDIDGYGGIALPELIATMFHTSGYDTQ-OH which is a variant of a fragment of human α-lactalbumin.

The peptide (700 μM), in lyophilised form, was added to a tube together with sodium oleate flakes (3.5 mM). Each tube was then reconstituted with required volume of either:

1) Phosphate Buffered Saline (NaCl 6.8 g/L;), $Na_2HPO_4 \times 2H_2O$ (4.8 g/L); and $KH_2PO_4$ (1.3 g/L) (pH 7.2).
2) NaCl solution (116 mM) (pH 7.01)
3) $Na_2HPO_4$ solution (31 mM) (pH 8.6)
4) $KH_2PO_4$ solution (9.56 mM) (pH 4.6)
5) A mixture of (2) and (4) (pH 4.63)
6) A mixture of (2) and (3) (pH 8.37)
7) A mixture of (3) and (4) (pH 7.29)

Each mixture was vortexed until the solution was clear. The complexes obtained were then lyophilised. The lyophilization conditions were a pressure below 1.2 mbar and a temperature below −55° C.

Each tube was stored at −20° C. or below and reconstituted by the addition of 30 mL sterile water shortly before use.

EXAMPLE 2

Cell Death Assay

Human lung carcinoma cells (A549, ATCC) were cultured in RPMI-1640 with non-essential amino acids (1:100), 1 mM sodium pyruvate, 50 μg/ml Gentamicin and 5-10% fetal calf serum (FCS) at 37° C., 5% $CO_2$. For cell death experiment, cells were grown on 96-well plate ($2 \times 10^4$/well, Tecan Group Ltd) overnight. Cells were incubated with biologically active complexes obtained in Example 1 at dosages equivalent to either 7, 21 or 35 μM peptide in serum-free RPMI-1640 at 37° C. FCS was added after 1 hour. Cell death was quantified 3 hours after peptide-oleate treatment by three biochemical methods including 1) estimation of cellular ATP levels using luminescence based ATPlite™ kit (Perkin Elmer) 2) Presto Blue fluorescence staining (Invitrogen, A13262) and 3) trypan blue exclusion assay. Fluorescence and luminescence were measured using a microplate reader (Infinite F200, Tecan).

Figure 1A:
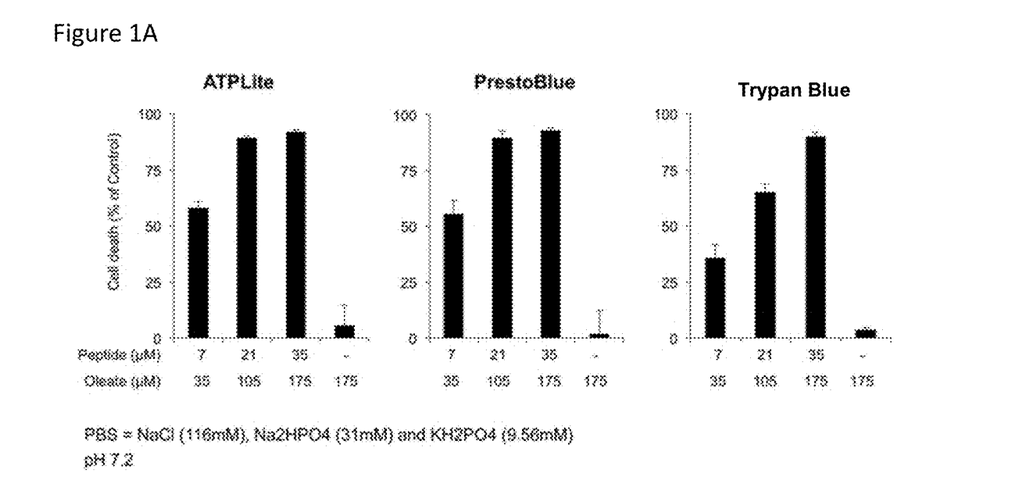
FIG. 1A shows the results of ATP Lite, PrestoBlue and Trypan Blue studies obtained using a range of biologically active complexes, prepared in PBS, on tumour cells.
Figure 1B:
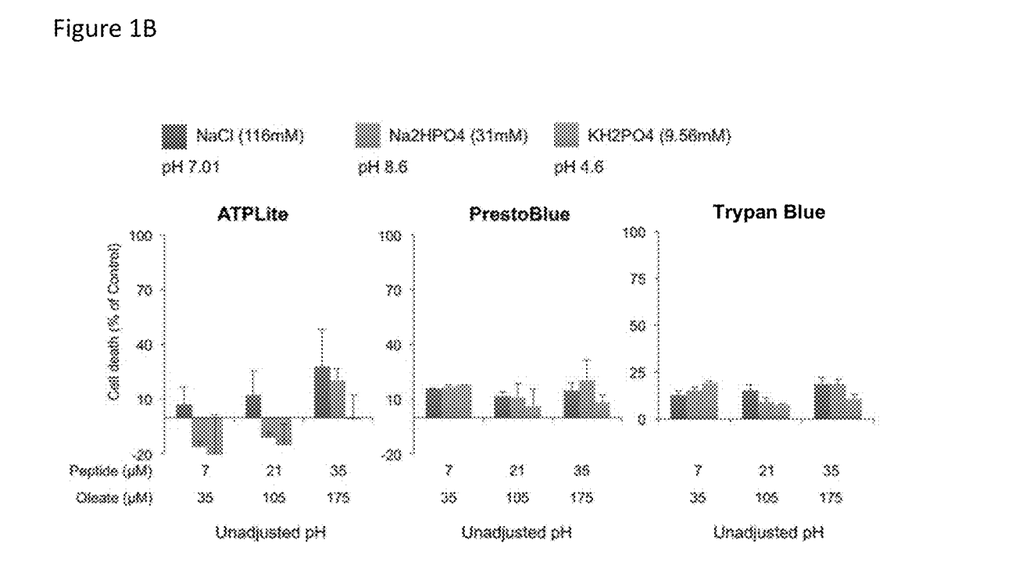
FIG. 1B shows results of ATP Lite, PrestoBlue and Trypan Blue studies obtained using a range of biologically active complexes, prepared in one salt of PBS, on tumour cells.
Figure 1C:
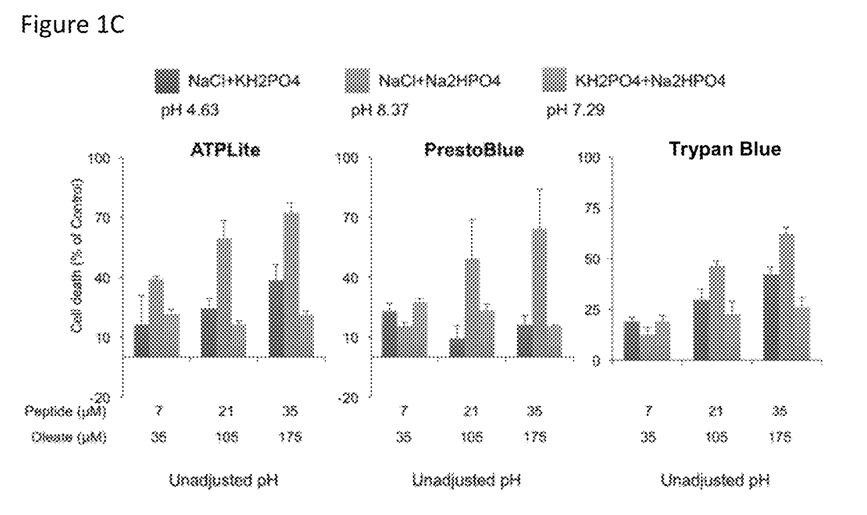
FIG. 1C presents results of ATP Lite, PrestoBlue and Trypan Blue studies obtained using a range of biologically active complexes, prepared in two salts of PBS, on tumour cells.

The results are shown in FIG. 1A-C. The complexes prepared in PBS were highly active and triggered cell death in a dose dependent manner (FIG. 1A). Those prepared with only a single salt of the PBS (FIG. 1B) showed a significant loss of activity. However, as shown in FIG. 1C, the mixture (6) above, maintained a reasonable level of tumour cell death activity in a dose dependent manner.

EXAMPLE 3

Effect of Filtration on Method

Figure 2:
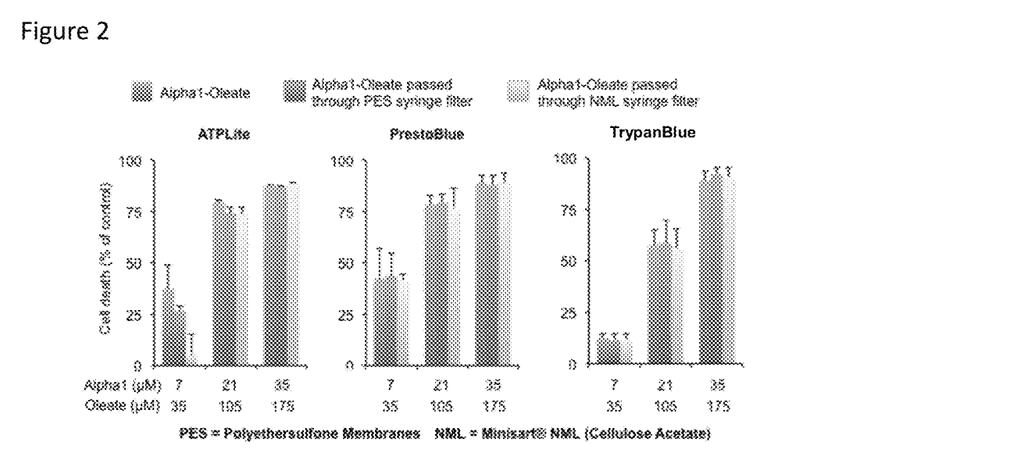
FIG. 2 shows a comparison of similar results obtained with and without filtration of the solutions.

The method of example 1 was repeated twice using the PBS solution (1) but in this case, each solution was passed through a chemically different filter, either Polyethersulfone membranes (Ser. No. 12/846,445, VWR) and Minisart® NML cellulose acetate Filters (60/810,103, Sartorius). The biological efficacy of the product was tested as described in Example 2 in a side-by-side comparison with product which had not been filtered. The results are shown in FIG. 2.

No significant difference was observed in the biological activity of the complex quantified by measuring total cellular ATP levels, PrestoBlue staining and Tryphan Blue exclusion assay.

EXAMPLE 4

Production of BAMLET

Figure 3A:
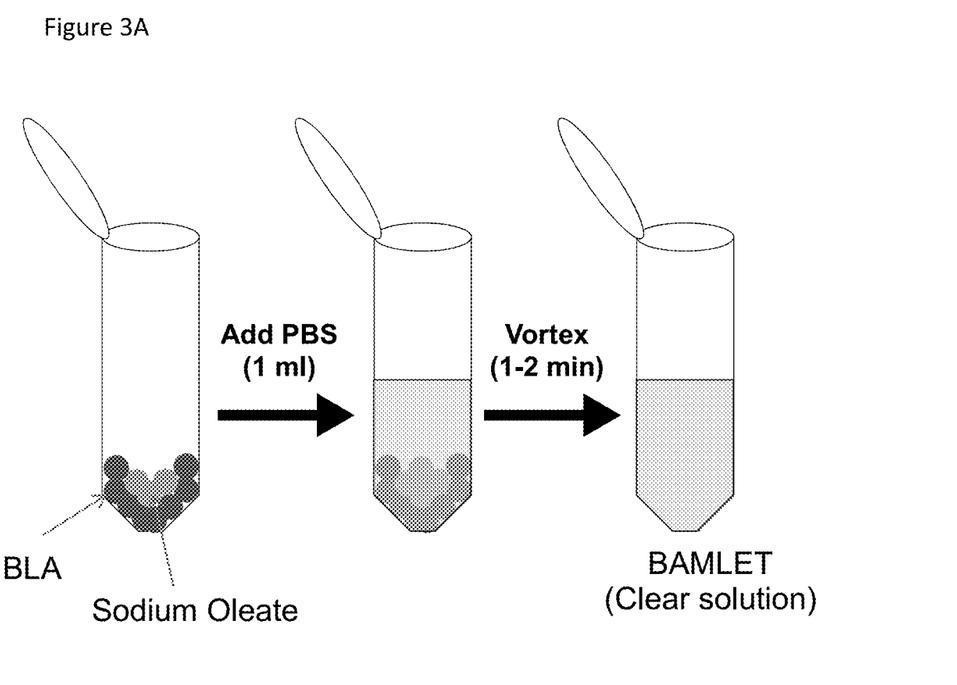
FIG. 3A shows a schematic photograph of the preparation of a complex comprising bovine alpha-lactalbumin.
Figure 3B:
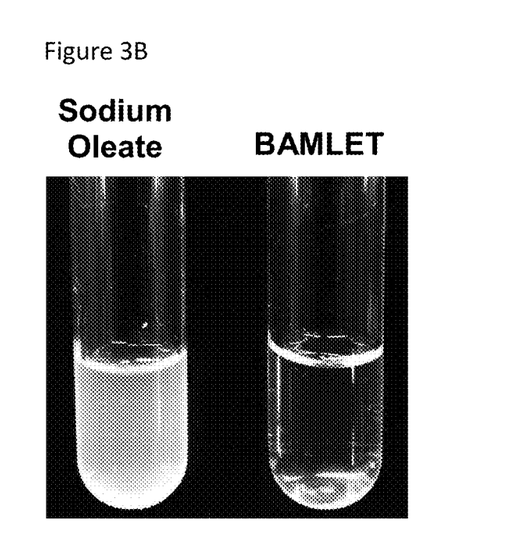
FIG. 3B shows photographs of tubes before and after vortexing.

Bovine alpha-lactalbumin (700 μM), in lyophilised form, was added to a tube together with sodium oleate flakes (3.5 mM. Phosphate Buffered Saline (1 ml) was then added to the tube which was vortexed at room temperature for 1-2 minutes. A clear solution formed (FIG. 3A-B)

Figure 4:
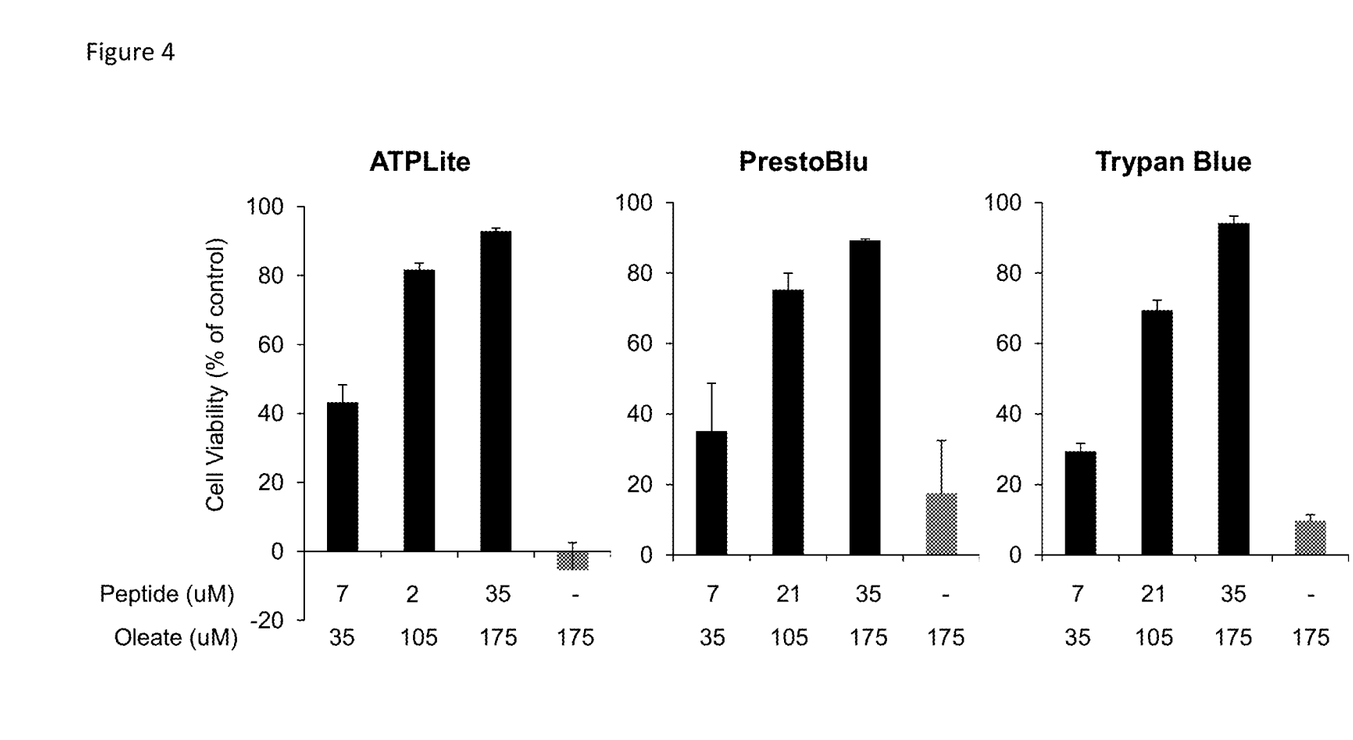
FIG. 4 shows results of ATP Lite, PrestoBlue and Trypan Blue studies of tumour cells to which the resultant solution was administered.

The resultant solution was tested using the assay described in Example 2. Results are shown in FIG. 4. It is clear that the solution was biologically active and killed A549 lung carcinoma cells in a dose dependent manner. This effect was transient, however, as lyophilisation of the complex removed the activity.

---

The invention claimed is:

1. A method for preparing a biologically active complex, said method comprising dissolving a mixture of a polypeptide element in powder form and oleic acid or a pharmaceutically acceptable salt thereof also in solid form, in an aqueous solvent comprising at least two salts to form an aqueous solution comprising a biologically active complex of the polypeptide element and oleic acid, wherein the first salt of the at least two salts is sodium chloride or potassium chloride and the second salt of the at least two salts is disodium phosphate or mono-potassium phosphate, wherein the method is performed at a moderate temperature of up to 50° C., and wherein the polypeptide element is:
(a) an alpha-lactalbumin or an alpha-lactalbumin having each of the cysteine residues replaced with another amino acid;
(b) a peptide fragment of an alpha-lactalbumin having up to 50 amino acids and comprising SEQ ID NO:1, SEQ ID NO:2, SEQ ID NO:6 or SEQ ID NO:7;
(c) a peptide fragment of a Coat Protein Complex II (COPII) family protein, wherein the peptide fragment has up to 50 amino acids and comprises SEQ ID NO:5; or
(d) a lysozyme.

2. The method of claim 1, wherein the aqueous solvent further comprises a third salt which is mono-sodium phosphate or mono-potassium phosphate.

3. The method of claim 1, wherein the moderate temperature is from 10-40° C.

4. The method of claim 1, wherein the moderate temperature is from 15-25° C.

5. The method of claim 1, further comprising filtering the aqueous solution formed.

6. The method of claim 1, further comprising removing the aqueous solvent and obtaining the biologically active complex in solid form.

7. The method of claim 6, wherein the aqueous solvent is removed by lyophilisation.

8. The method of claim 1, wherein the polypeptide element is an alpha-lactalbumin.

9. The method of claim 8, wherein the polypeptide element is a bovine alpha-lactalbumin.

10. The method of claim 1, wherein the first salt is sodium chloride and the second salt is disodium phosphate.

11. The method according of claim 2, wherein the third salt is mono-potassium phosphate.

* * * * *

SEQUENCE LISTING

```
<160> NUMBER OF SEQ ID NOS: 7

<210> SEQ ID NO 1
<211> LENGTH: 40
<212> TYPE: PRT
<213> ORGANISM: Artificial Sequence
<220> FEATURE:
<223> OTHER INFORMATION: Mutated protein fragment
<220> FEATURE:
<221> NAME/KEY: MISC_FEATURE
<222> LOCATION: (6)..(6)
<223> OTHER INFORMATION: any amino acid other than Cys
<220> FEATURE:
<221> NAME/KEY: MISC_FEATURE
<222> LOCATION: (28)..(28)
<223> OTHER INFORMATION: any amino acid other than Cys

<400> SEQUENCE: 1

Lys Gln Phe Thr Lys Xaa Glu Leu Ser Gln Leu Leu Lys Asp Ile Asp
1               5                   10                  15

Gly Tyr Gly Gly Ile Ala Leu Pro Glu Leu Ile Xaa Thr Met Phe His
            20                  25                  30

Thr Ser Gly Tyr Asp Thr Gln Ala
        35                  40

<210> SEQ ID NO 2
<211> LENGTH: 43
<212> TYPE: PRT
<213> ORGANISM: Artificial Sequence
<220> FEATURE:
<223> OTHER INFORMATION: Mutated protein fragment
<220> FEATURE:
<221> NAME/KEY: MISC_FEATURE
<222> LOCATION: (11)..(11)
<223> OTHER INFORMATION: any amino acid other than Cys
<220> FEATURE:
<221> NAME/KEY: MISC_FEATURE
<222> LOCATION: (31)..(31)
<223> OTHER INFORMATION: any amino acid other than Cys
<220> FEATURE:
<221> NAME/KEY: MISC_FEATURE
<222> LOCATION: (40)..(40)
<223> OTHER INFORMATION: any amino acid other than Cys

<400> SEQUENCE: 2

Leu Asp Asp Asp Ile Thr Asp Asp Ile Met Xaa Ala Lys Lys Ile Leu
1               5                   10                  15

Asp Ile Lys Gly Ile Asp Tyr Trp Leu Ala His Lys Ala Leu Xaa Thr
            20                  25                  30

Glu Lys Leu Glu Gln Trp Leu Xaa Glu Lys Leu
        35                  40
```

<210> SEQ ID NO 3
<211> LENGTH: 40
<212> TYPE: PRT
<213> ORGANISM: Artificial Sequence
<220> FEATURE:
<223> OTHER INFORMATION: Mutated protein fragment

<400> SEQUENCE: 3

Lys Gln Phe Thr Lys Ala Glu Leu Ser Gln Leu Leu Lys Asp Ile Asp
1               5                   10                  15

Gly Tyr Gly Gly Ile Ala Leu Pro Glu Leu Ile Ala Thr Met Phe His
            20                  25                  30

Thr Ser Gly Tyr Asp Thr Gln Ala
        35                  40

<210> SEQ ID NO 4
<211> LENGTH: 43
<212> TYPE: PRT
<213> ORGANISM: Artificial Sequence
<220> FEATURE:
<223> OTHER INFORMATION: Mutated protein fragment

<400> SEQUENCE: 4

Leu Asp Asp Asp Ile Thr Asp Ile Met Ala Ala Lys Lys Ile Leu
1               5                   10                  15

Asp Ile Lys Gly Ile Asp Tyr Trp Leu Ala His Lys Ala Leu Ala Thr
            20                  25                  30

Glu Lys Leu Glu Gln Trp Leu Ala Glu Lys Leu
        35                  40

<210> SEQ ID NO 5
<211> LENGTH: 23
<212> TYPE: PRT
<213> ORGANISM: Artificial Sequence
<220> FEATURE:
<223> OTHER INFORMATION: Protein fragment

<400> SEQUENCE: 5

Met Ala Gly Trp Asp Ile Phe Gly Trp Phe Arg Asp Val Leu Ala Ser
1               5                   10                  15

Leu Gly Leu Trp Asn Lys His
            20

<210> SEQ ID NO 6
<211> LENGTH: 39
<212> TYPE: PRT
<213> ORGANISM: Artificial Sequence
<220> FEATURE:
<223> OTHER INFORMATION: Mutated protein fragment
<220> FEATURE:
<221> NAME/KEY: MISC_FEATURE
<222> LOCATION: (6)..(6)
<223> OTHER INFORMATION: any amino acid other than Cys
<220> FEATURE:
<221> NAME/KEY: MISC_FEATURE
<222> LOCATION: (28)..(28)
<223> OTHER INFORMATION: any amino acid other than Cys

<400> SEQUENCE: 6

Lys Gln Phe Thr Lys Xaa Glu Leu Ser Gln Leu Leu Lys Asp Ile Asp
1               5                   10                  15

Gly Tyr Gly Gly Ile Ala Leu Pro Glu Leu Ile Xaa Thr Met Phe His
            20                  25                  30

-continued

```
Thr Ser Gly Tyr Asp Thr Gln
        35

<210> SEQ ID NO 7
<211> LENGTH: 39
<212> TYPE: PRT
<213> ORGANISM: Artificial Sequence
<220> FEATURE:
<223> OTHER INFORMATION: Mutated protein fragment

<400> SEQUENCE: 7

Lys Gln Phe Thr Lys Ala Glu Leu Ser Gln Leu Leu Lys Asp Ile Asp
1               5                   10                  15

Gly Tyr Gly Gly Ile Ala Leu Pro Glu Leu Ile Ala Thr Met Phe His
            20                  25                  30

Thr Ser Gly Tyr Asp Thr Gln
        35
```